United States Patent [19]

Loesch et al.

[11] Patent Number: 5,573,728
[45] Date of Patent: Nov. 12, 1996

[54] DEVICE FOR SELECTIVE DETECTION OF GAS

[75] Inventors: Muriel Loesch, Paris; Francis Menil, La Brede; Claude Lucat, Cestas; Pascale Dutronc, Paris; Véronique Marteau, Survilliers, all of France

[73] Assignee: Gaz de France, Paris, France

[21] Appl. No.: 185,806

[22] PCT Filed: Jun. 4, 1993

[86] PCT No.: PCT/FR93/00534

§ 371 Date: Jan. 28, 1994

§ 102(e) Date: Jan. 28, 1994

[87] PCT Pub. No.: WO93/24827

PCT Pub. Date: Dec. 9, 1993

[30] Foreign Application Priority Data

Jun. 4, 1992 [FR] France .................................. 92 06791

[51] Int. Cl.6 .......................... G01N 27/04; G01N 27/14; G01N 27/16
[52] U.S. Cl. .......................... 422/90; 73/23.21; 73/23.31; 73/31.06; 422/94; 422/98
[58] Field of Search .................... 422/94, 90, 98, 422/119, 80; 436/141, 143, 145; 340/634; 73/27, 23.21, 23.31, 31.06

[56] References Cited

U.S. PATENT DOCUMENTS

| 4,443,791 | 4/1984 | Risgin ........................... 340/634 |
| 4,457,161 | 7/1984 | Iwanaga ......................... 73/23 |
| 4,541,988 | 9/1985 | Tozier ........................... 422/94 |
| 4,847,783 | 7/1989 | Grace ........................... 364/497 |
| 4,911,892 | 3/1990 | Grace ........................... 422/94 |
| 5,047,214 | 9/1991 | Fukui ........................... 422/98 |
| 5,400,643 | 3/1995 | De Angelis ..................... 73/31.06 |

FOREIGN PATENT DOCUMENTS

| 0313390 | 4/1989 | European Pat. Off. . |
| 0444753 | 9/1991 | European Pat. Off. . |
| 2002907 | 8/1978 | United Kingdom . |

OTHER PUBLICATIONS

Abstract of Publication No. JP56054348 (Kimetake et al.).
Patent Abstracts of Japan, vol. 13, No. 32 (P–817) 25 Janvier 1989.
Patent Abstracts of Japan, vol. 9, No. 129 (P–361) Juin (1985).
EP, A, 0 313 390 (Toshiba) (1989).

Primary Examiner—Jill Warden
Assistant Examiner—Jan M. Ludlow
Attorney, Agent, or Firm—Shenier & O'Connor

[57] ABSTRACT

A device for selective detection of gas, enabling a first gas to be detected relative to a second gas, the device having a solid state sensor provided with an insulating substrate having a first face and a second face, a heater element deposited on the first face of said substrate, metal electrodes deposited on the second face of said substrate, and a semiconductor layer formed on said electrode and over the second face of said substrate. Detection is performed by simultaneously determining a voltage U representative of the resistance of the semiconductor element of the solid state sensor and the voltage difference S between a voltage representative of the temperature of the heater element of said solid state sensor and a voltage representative of the temperature of a heater element of a reference sensor, the voltage U and the voltage difference S each being compared with a different and predetermined threshold voltage in order to enable selective detection of gas.

17 Claims, 4 Drawing Sheets

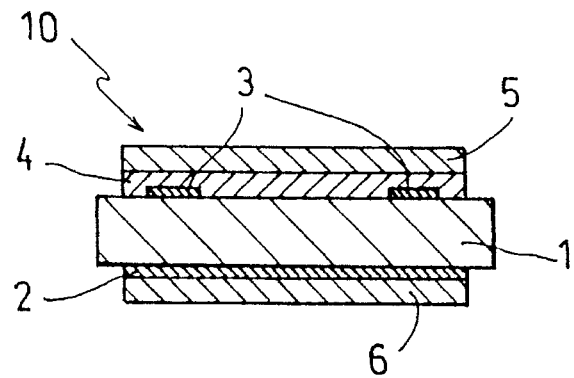
Fig_1
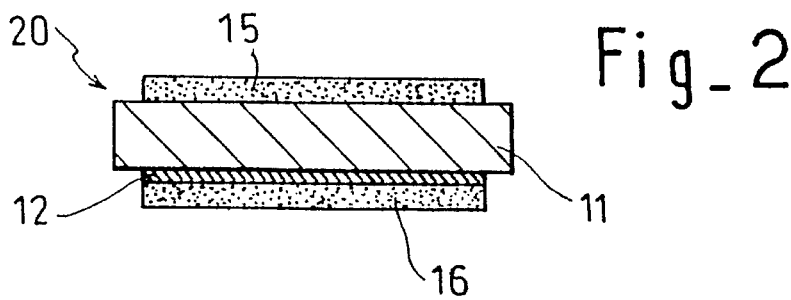
Fig_2
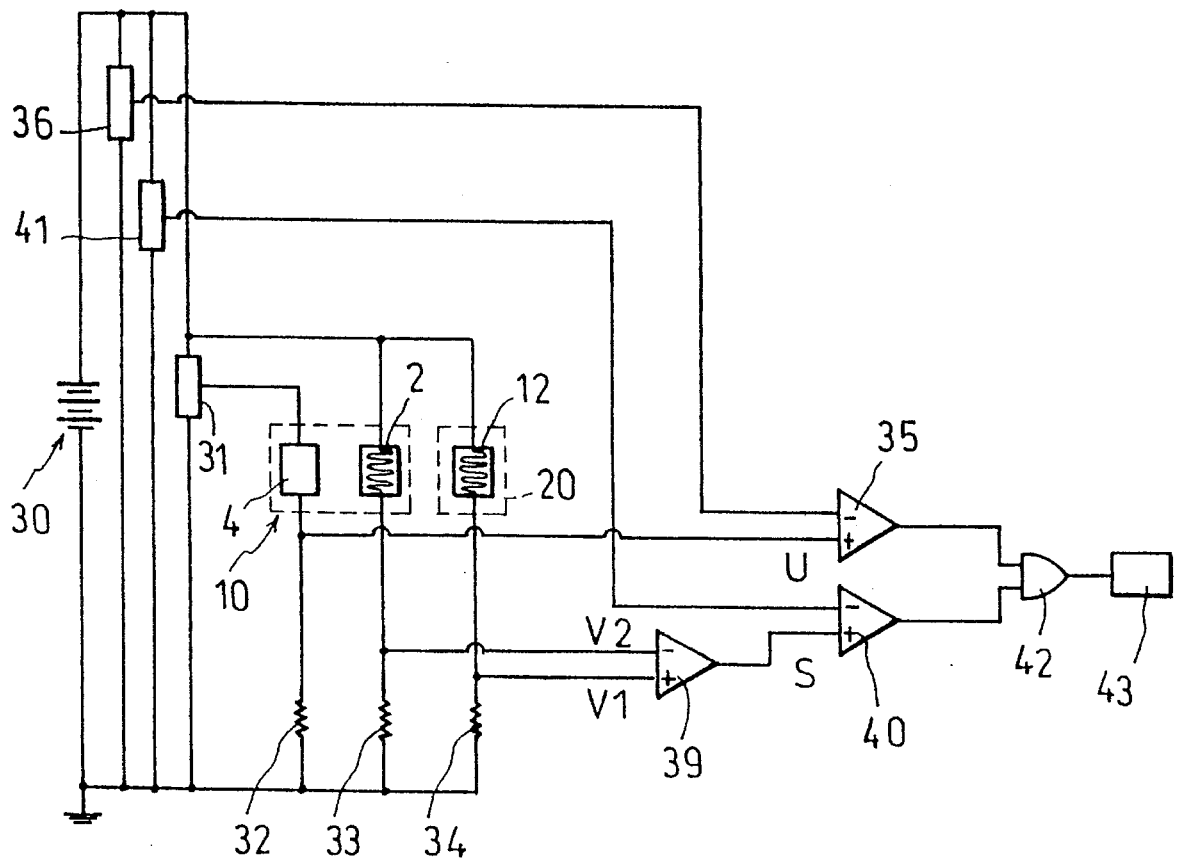
Fig_3

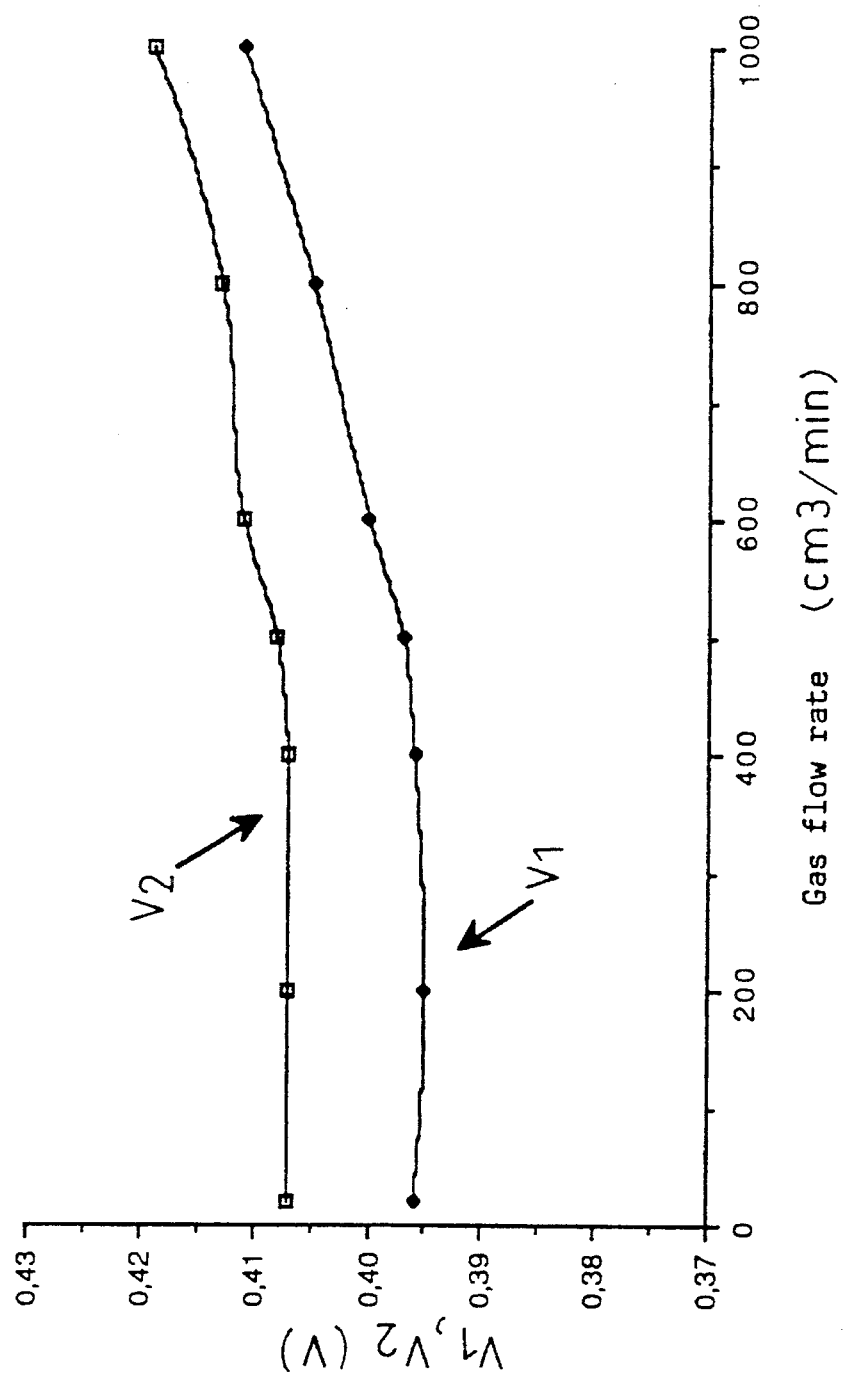
Fig_4

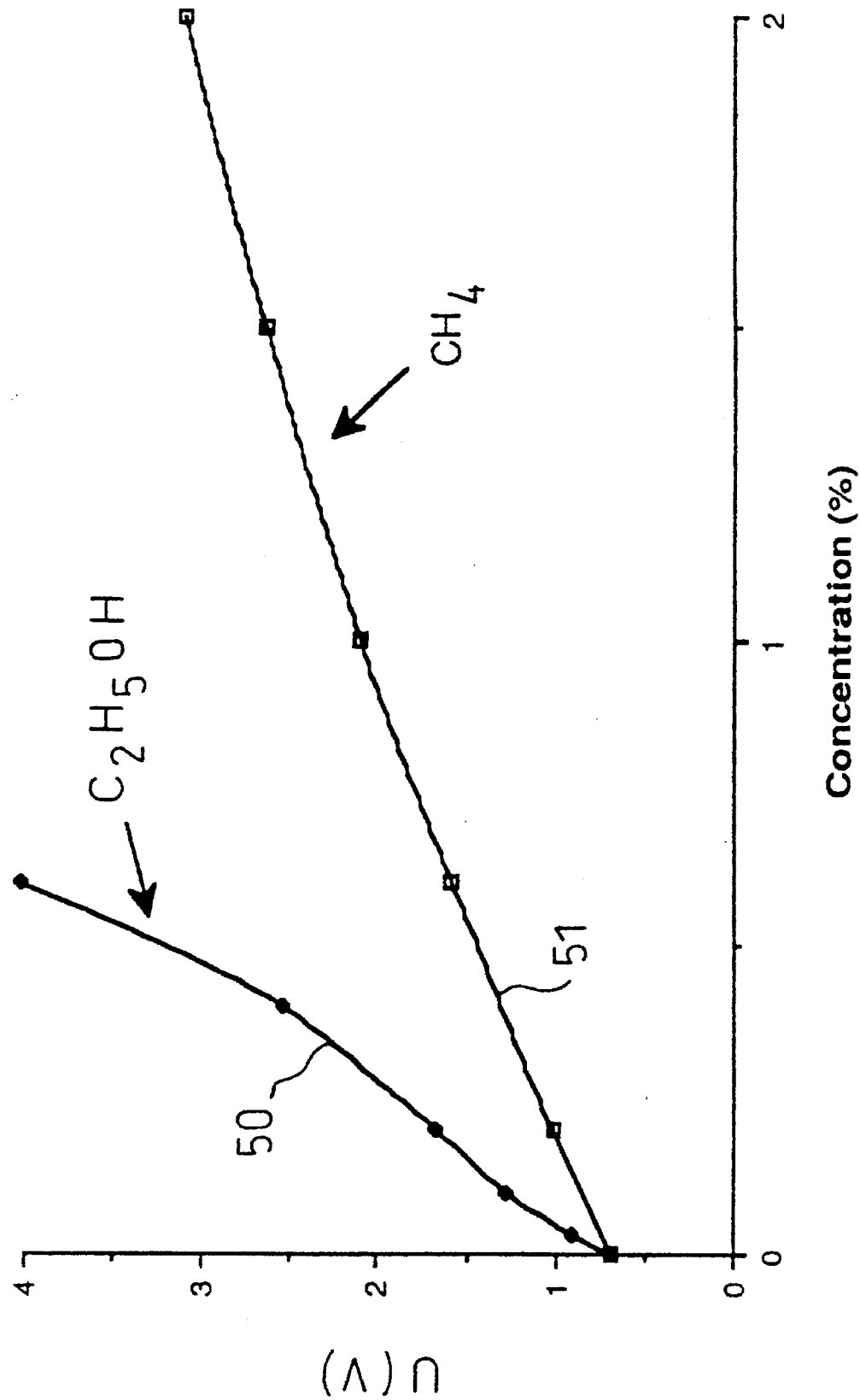

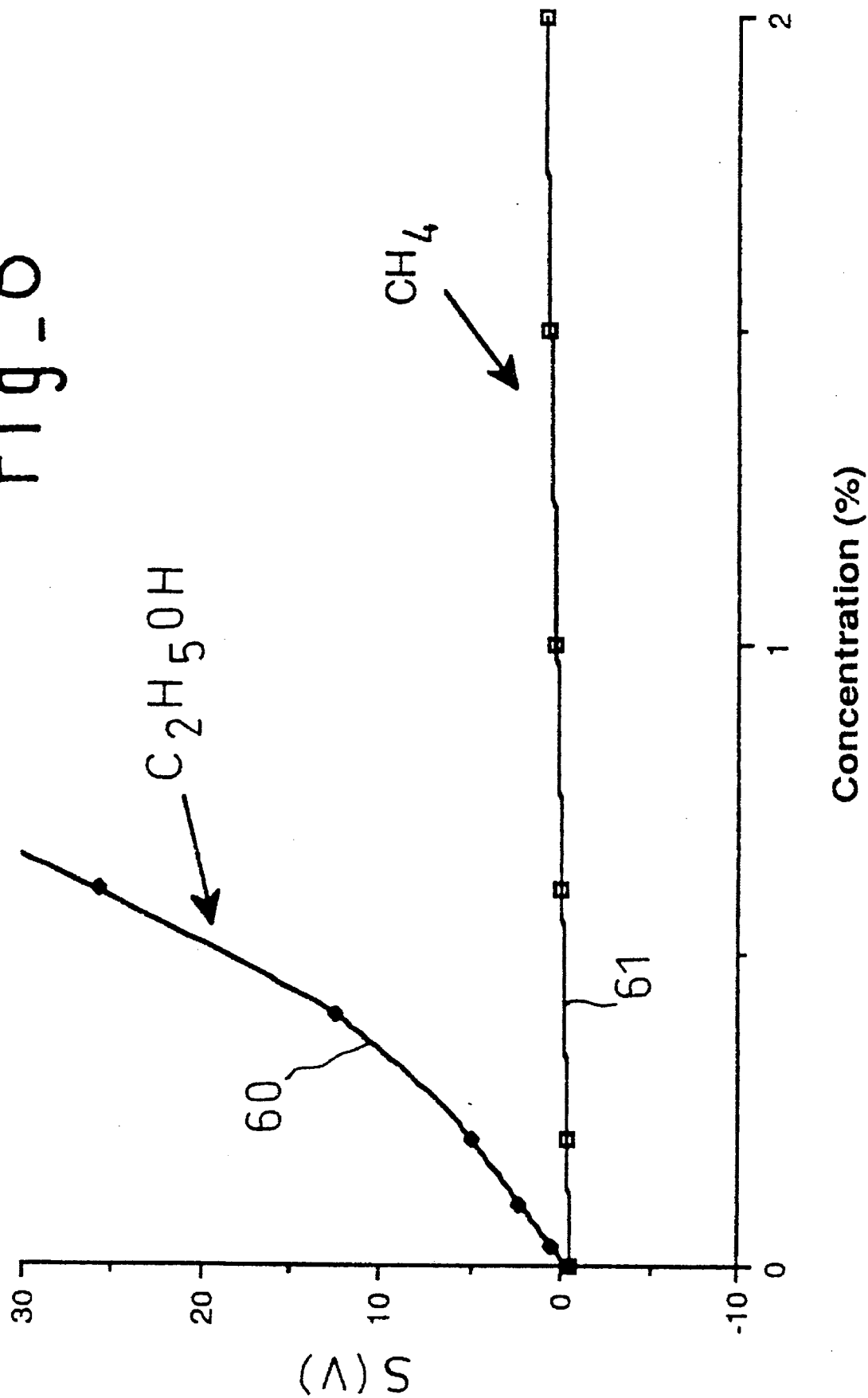
Fig_6

DEVICE FOR SELECTIVE DETECTION OF GAS

The present invention relates to a device for selectively detecting a gas present in ambient air, and it is mainly intended for safety applications, particularly detecting leaks from networks and from assemblies that implement such a gas.

BACKGROUND OF THE INVENTION

Conventionally, when using solid state sensors, in particular semiconductors, gas detection is based on variation in the resistance of a semiconductor metal oxide such as $SnO_2$ in the presence of a reducing gas, which variation can be related to the concentration of the gas.

However, such a method suffers from the drawback of not discriminating properly between reducing gases.

In order to improve the selectivity of such sensors, it is known to associate a catalyst with the semiconductor element constituting the sensor, the catalyst being constituted by a noble metal such as platinum or palladium, and being present at a concentration that does not exceed 1% of the weight of the oxide.

It is also known that the response of such sensors can be improved by varying the temperature to which they are raised by means of a platinum resistance element integrated in the sensor and serving to heat it.

Nevertheless, neither of those improvements to the preceding method provides a solution that is completely satisfactory, which is why suggestions have been made to use the variation in the temperature of the sensor due to the heat given off by combustion of the gas in addition to measuring conductance.

Unfortunately, implementing such a method turns out to be particularly difficult since the temperature of the sensor depends not only on the heat from the reaction, but also on variations in ambient temperature or on gas flow conditions relating to speed and direction which can give rise to temperature variations in the sensor that are of the same order of magnitude as those associated with the combustion of the gas.

OBJECTS AND SUMMARY OF THE INVENTION

An object of the invention is to provide a gas detection device that is both simple and reliable, that enables variations in ambient temperature to be compensated, and that amplifies the variation in the temperature of the sensor that is due to the combustion of the gas.

Another object of the invention is to implement a device that is not sensitive to the flow conditions of the gas acting on the solid state sensor constituting an element of the device, or at any rate that is relatively insensitive thereto.

These objects are achieved by a device for selective detection of gas, enabling a first gas to be detected relative to a second gas, the device comprising a solid state sensor provided with an insulating substrate having a first face and a second face, a heater element deposited on the first face of said substrate, metal electrodes deposited on the second face of said substrate, and a semiconductor layer formed on said electrode and over the second face of said substrate, wherein detection is performed by simultaneously determining a voltage U representative of the resistance of the semiconductor element of the solid state sensor and the voltage difference S between a voltage representative of the temperature of the heater element of said solid state sensor and a voltage representative of the temperature of a heater element of a reference sensor, said voltage U and said voltage difference S each being compared with a different and predetermined threshold voltage in order to enable selective detection of gas.

The temperature difference between the solid state sensor and the reference sensor due to the combustion of the gas gives a simple image of the concentration of the gas that needs subsequently merely to be combined with the variation in the resistance of the solid state sensor in order to make it possible to perform said selection between the two gases that may interact with said sensors.

Advantageously, the semiconductor layer of the solid state sensor is provided with a catalyst constituting more than 1% but not more than 20% by weight thereof.

This considerable increase in the quantity of catalyst used, which quantity usually does not exceed a threshold of 1% by weight in practice, makes it possible in surprising manner to obtain a considerable improvement in the selectivity of the solid state sensor due to the rise in temperature achieved by the catalyst, even at low concentrations of gas. Similarly, it considerably increases sensitivity to the gas to be detected.

Preferably, the semiconductor layer of the solid state sensor is covered by an insulating porous deposit.

Implementation of an insulating porous deposit serves to preheat the combustible gas to the operating temperature of the sensor, and thus very considerably improves the sensitivity of such a solid state sensor by increasing the fraction of the gas that participates in the reaction. Furthermore, by isolating the semiconductor element from the flow of gas, the influence of gas flow conditions is also considerably limited.

Similarly, the solid state sensor may also include an insulating layer covering the heater element and the first face of said substrate.

This additional porous layer optionally including a catalyst such as 1% to 20% by weight of platinum or of palladium, enables yet more heat to be given off and thus improves the performance of the sensor.

The mixing and multilayer technology methods used enable a product to be created that has a large catalyst content without that destroying its semiconductive properties.

Advantageously, the reference sensor which does not have the catalyst is made using technology identical to that used for making said solid state sensor and it includes an insulating substrate having first and second faces, and a heater element deposited on the first face of said substrate, said parts being of dimensions identical to those of the solid state sensor.

Similarly, the reference sensor may include a catalyst-free insulating layer covering the heater element and the first face of said substrate if said solid state sensor also includes such an additional insulating layer.

The second face of said substrate preferably also includes a second insulating layer.

Thus, both sensors interchange heat with the external medium in similar manner and it is easier to distinguish the effect due solely to the gas.

According to a particular characteristic, the threshold voltages and the power supply voltages of the semiconductor element and of the heater elements are derived from a single reference source.

The use of a single power supply source for the entire device makes it possible in this case further to limit external influences (fluctuations of the single source) in that they are then identical and have the same effects on all of the components.

Each of the heater elements is disposed in a respective branch of a resistor bridge powered by the single reference source and delivering the voltage difference S via an amplifier.

A visible or audible alarm is triggered whenever one of the predetermined threshold voltages is crossed without the other one being crossed as well.

BRIEF DESCRIPTION OF THE DRAWINGS

Other advantages and characteristics of the present invention will appear more clearly from the following description given by way of non-limiting example and made with reference to the accompanying drawings, in which:

FIG. 1 shows a solid state sensor implemented in a detection device of the invention;

FIG. 2 shows a reference sensor co-operating with the sensor of FIG. 1;

FIG. 3 is a block diagram of the device of the invention for selective detection of gas and including the sensors of FIGS. 1 and 2;

FIG. 4 is a graph showing the appearance of characteristic signals from FIG. 3 as a function of gas flow rate; and FIGS. 5 and 6 are graphs showing how the signals provided by the FIG. 3 device vary as a function of gas concentration in two different gaseous mediums.

MORE DETAILED DESCRIPTION

FIG. 1 shows a gas sensor 10 of the solid state type.

This multilayer sensor comprises a plurality of elements:

an insulating substrate 1, preferably made of alumina, e.g. in the form of a rectangular block, having a top face and a bottom face;

a heater element or heater 2 deposited on one of the faces of the substrate by silkscreen printing, and, for example, being sinuous in shape;

interdigitated metal electrodes 3 deposited on the other face of the substrate by thick film or by thin film technology;

a semiconductor layer 4 formed by thick film or by thin film technology over the electrodes and said other face of the substrate; and a deposit 5 based on porous alumina and covering the semiconductor layer.

In order to avoid any interaction between the semiconductor element 4 and the metal electrodes 3, the metal electrodes are made of a noble metal that is stable at high temperature, such as platinum or gold, and the semiconductor element is preferably based on $SnO_2$.

Advantageously, an additional insulating deposit 6 covers the heater element 2 and the face of the substrate on which it is deposited.

The assembly is mounted on a support (not shown) enabling the heater element and the metal electrodes to be connected to two electrical circuits of a detection device whose structure and operation are described below.

The use firstly of the variation in the resistance of the semiconductor layer 4 due to interaction with the reducing gas, and secondly of variation in the temperature of the sensor 10 due to the heat given off by combustion of the gas turns out to be impossible when the sensor is operated at the same temperature as the ambient medium. The sensor will generally be placed either in a room in industrial premises, e.g. a boiler room, or else. in domestic premises such as a kitchen, and in either case the sensor is intended to ensure safety for people and for property.

Thus, when detecting methane ($CH_4$) selectively relative to ethanol ($C_2H_5OH$) it can be estimated that variations in the temperature and the resistance of the device are meaningful only above 300° C. That is why the sensor has a heater 2 enabling its temperature to be maintained in a range running from 350° C. to 550° C.

It should also be noted that this temperature range may naturally be different when detecting gases other than those mentioned above.

One of the roles of the deposit 5 based on porous alumina is to preheat the combustible gas to the working temperature defined by the power supplied to the heater element 2. Another role of said deposit is to ensure selective combustion of the gas in association with the different combustion temperatures of the gases. Thus, when selectively detecting methane relative to ethanol, the deposit causes partial combustion of the alcohol to take place before it reaches the semiconductor, thus enabling a large amount of heat to be given off and a reduction in the signal from the semiconductor, which does not happen with methane.

In addition, this porous alumina layer 5 avoids the gas acting directly on the-semiconductor layer 4, where such direct action is highly disturbing to measurement. It is difficult to control the gas that reacts with the sensor since the gas can be presented with flow conditions of speed and of direction that are highly variable. By reducing the thermal variations due to external fluctuations in the flow, the layer 5 increases the selectivity of the sensor, thus enabling excellent correlation to be obtained between variation in the temperature of the semiconductor and combustion of the gas, in particular of ethanol.

In order to further improve the selectivity of the sensor, and in particular at low concentrations of gas, the semiconductor element 4 and the insulating porous deposits 5 and 6 may receive a catalyst constituted by a noble material such as platinum or palladium, and the catalyst of the semiconductor element may be different from that of the porous deposit. Preferably, the porous deposits are provided with platinum and the semiconductor element with palladium. Nevertheless, whereas the concentration of such an additive is normally less than 1% by weight, in the method of the invention, the additive constitutes 1% to 20% by weight. Surprisingly, the selectivity of the sensor is greatly improved under the effect of the gas-dependent temperature rise caused by such addition, and similarly its sensitivity to the gas to be detected is considerably increased. The catalyst is distributed within the semiconductor by dispersion so that the semiconductor retains its semiconductive properties in spite of the high percentage of catalyst that it contains.

Since the temperature variations due to fluctuations in ambient temperature are of the same order of magnitude as temperature variations due to combustion of the gas, it is necessary to make the detection device so that it is as insensitive as possible to such external influences. In this context, the detection device of the invention includes, in addition to the above-mentioned solid state sensor 10, a reference sensor 20 which is implemented using the same technology and which has dimensions that are analogous to those of the measurement sensor 10.

FIG. 2 shows such a reference sensor that comprises:

an insulating substrate 11, preferably made of alumina, and having a top face and a bottom face; and a heater element or heater 12 deposited on one of the faces of the substrate by silkscreen printing and being sinuous in shape.

Optionally, when the solid state sensor 10 includes an insulating layer 6 covering the heater element and the corresponding face of the substrate, the reference sensor is also provided with an additional insulating layer 16, e.g. made of glass, covering the heater element 12 and the face of the substrate on which said heater element is deposited. In order to further improve the similarity of behavior relative to ambient temperature or to gas flow around the two sensors, a second insulating layer 15 may be deposited on the other face of the substrate of the reference sensor 20. The thickness of said layer is determined so that both sensors have identical thermal responses to variations in ambient temperature. The assembly created in this way is mounted in the support that also contains the sensor 10, and it is connected to another electrical circuit of the detection device.

This structure which is identical in terms of geometry and manufacturing technology between the reference sensor 20 and the solid state sensor 10, the reference sensor merely lacking the semiconductor element, makes it possible to reduce sensitivity to temperature fluctuations in the external atmosphere and also to flow, thereby facilitating measurement by means of the detection device.

It should be observed that in order to distinguish more clearly between the effect of gas combustion on the two sensors, the additional layers 15 and 16 (when present on the reference sensor 20) should have no catalystic properties, unlike the insulating layers 5 and 6 of the solid state sensor 10.

The block diagram of FIG. 3 corresponds to an implementation of the detection device of the invention for performing selective detection of methane relative to ethanol by implementing the above-described reference sensor and solid state sensor, and consisting in determining firstly the resistance of the semiconductor layer 4 and secondly the temperature difference between the solid state sensor 10 and the reference sensor 20 under the effect of gas combustion.

Firstly, it is important to note that the device is powered by a single reference source 30 from which the various reference voltages required for operation thereof are derived. This single power supply serves to limit external influences which are then identical for all of the components. Thus, the semiconductor element 4 of the solid state sensor 10 is powered via a first load resistor stage 32 from a voltage reference 31 derived from the single reference source 30. Similarly, the heater elements 2 and 12 of the solid state sensor 10 and of the reference sensor 20 are powered directly from the single reference source 30 via respective load resistors 33 and 34.

In order to obtain a nominal operating temperature close to 450° C. (i.e. the middle of the above-defined range 350° C. to 550° C.), and depending on the resistances of the load resistors, power may be provided at 15 V to 20 V, thus enabling a compact device to be implemented.

A first measurement signal U is obtained from the terminals of the first load resistor 32. This signal varies as a function of the resistance of the semiconductor element 4 and is compared by means of a first comparator 35 with a first threshold voltage delivered by a voltage reference 36 derived from the single power supply source 30.

A second measurement signal S is obtained from a voltage difference that exists between a voltage V2 taken from the terminals of the second load resistor 33 and that varies as a function of the temperature of the heater element 2 of the solid state sensor 10, and a voltage V1 taken from the terminals of the third load resistor 34 and that varies as a function of the temperature of the heater element 12 of the reference sensor 20. The voltages taken from the terminals of the load resistors 33 and 34 are applied to the inputs of an instrumentation amplifier 39 which obtains the difference $S=k(V1-V2)$.

The signal S is then compared by means of a second comparator 40 with a second threshold voltage delivered by a voltage reference 41 likewise derived from the single reference source 30.

A logic AND circuit 42 receives the outputs from the two comparators 35 and 40 and delivers a signal for a visible or audible alarm 43.

In the presence of a combustible gas, the resistance of the semiconductor element varies and the heat given off by the combustion of the gas gives rise to a change in the temperature of the heater element 2 of the solid state sensor 10, whereas the gas is not subject to any combustion at the reference sensor. In contrast, the temperature variations of the heaters 2 and 12 due to causes other than the heat of reaction between the gas and the sensor, i.e. relating to the temperature and the flow of the gas, are similar for both sensors.

FIG. 4 shows variations in the voltages V1 and V2 at the heater elements for a variable gas flow rate. It can be seen that the voltage variations in each of the two sensors are small and comparable, particularly at high flow rates.

FIGS. 5 and 6 show the characteristics of the measurement signals U and F for two types of gas, namely methane $CH_4$ and ethanol $C_2H_5OH$. The concentrations given are by volume.

When selectively detecting methane relative to ethanol, the heat given off is much larger in the presence of said ethanol 60 than in the presence of methane 61, as shown in FIG. 6. Furthermore, the resistance of the semiconductor element as shown by curves 50 and 51 is modified for said two gases (FIG. 5). It is thus easy to understand that by adjusting the first and second threshold voltages, it is possible to cause the visible or audible alarm 43 to be triggered if both the following conditions are satisfied: the voltage U that depends on the resistance of the semiconductor is greater than a first threshold defined by the voltage reference 36, and the differential voltage S that depends on the temperature increase due to the gas is less than a second threshold defined by the voltage reference 41.

The present invention is thus particularly suitable for selectively detecting methane relative to ethanol, as described above, but it is clearly not limited to those two gases only, and is applicable to any other gases that give off measurable amounts of heat.

We claim:

1. A device for selective detection of gas, enabling a first gas to be detected relative to a second gas, one of said gases being combustible, the device comprising a solid state sensor provided with an insulating substrate having a first face and a second face, a heater element disposed on the first face of said substrate, and a semiconductor layer formed on the second face of said substrate, the semiconductor layer having a resistance which varies in the presence of one of said gases; a reference sensor provided with an insulting substrate having a first face and a second face and a heater element disposed on the first face of said substrate; means for determining a voltage U representative of the resistance of the semiconductor layer of the solid state measurement sensor; means passing sufficient current through the heater elements to permit combustion of said combustible gas; means for determining the voltage difference S between a voltage representative of the temperature of the heater element of said solid state measurement sensor and a voltage representative of the temperature of the heater element of the reference sensor; means providing a first threshhold voltage; means providing a second threshold voltage; first means for comparing the voltage U with the first threshhold voltage; and second means for comparing the voltage difference S with the second threshold voltage.

2. A device according to claim 1, wherein the semiconductor layer of the solid state measurement sensor is provided with a catalyst constituting more than 1% but not more than 20% by weight thereof.

3. A device according to claim 1, wherein the sensors are made using multilayer technology.

4. A device according to claim 1, wherein said threshold voltages are derived from a single reference source.

5. A device according to claim 1, wherein the current passing means comprises means disposing the heater elements in respective branches of a resistance bridge powered from a single reference source.

6. A device according to claim 1 wherein the second face of the reference sensor is covered by an insulating layer having such thickness that the heating elements of the sensors have identical thermal responses to variations in ambient temperature.

7. A device according to claim 1, further including means responsive to the first and second comparing means for providing an alarm when one of the first and second threshold voltages is crossed.

8. A device according to claim 1, wherein said reference sensor further includes a catalyst-free insulating layer covering the heater element.

9. A device according to claim 8, wherein the insulating layer of the reference sensor is made of glass.

10. A device according to claim 1, wherein said reference sensor further includes a catalyst-free insulating layer covering the second face of said substrate.

11. A device according to claim 10 wherein the insulating layer of the reference sensor is made of glass.

12. A device according to claim 1, wherein said solid state measurement sensor also includes an porous insulating deposit deposited on the semiconductor layer.

13. A device according to claim 12, wherein the insulating deposit is constituted by alumina.

14. A device according to claim 12, wherein the insulating deposit is provided with a catalyst constituting more than 1% but more than 20% by weight thereof.

15. A device according to claim 1, wherein the measurement sensor further includes an insulating layer covering the heater element.

16. A device according to claim 15 wherein the insulating layer is provided with a catalyst constituting more than 1% but not more than 20% by weight thereof.

17. A device according to claim 15 wherein the insulating layer is constituted by alumina.

* * * * *

UNITED STATES PATENT AND TRADEMARK OFFICE
CERTIFICATE OF CORRECTION

PATENT NO. : 5,573,728
DATED : Nov. 12, 1996
INVENTOR(S) : Muriel Loesch, Francis Menil, Claude Lucat, Pascale Dutronc, Veronique Marteau It is certified that error appears in the above-identified patent and that said Letters Patent is hereby corrected as shown below:

Column 6, line 57 - after "state" insert -- measurement --.

Column 6, line 63 - "insulting" should read -- insulating --.

Column 8, line 20 - after "but" insert -- not --.

Signed and Sealed this

Twenty-eighth Day of January, 1997

Attest:

BRUCE LEHMAN

*Attesting Officer*   *Commissioner of Patents and Trademarks*